(12) United States Patent
Matsumoto

(10) Patent No.: US 6,527,709 B2
(45) Date of Patent: Mar. 4, 2003

(54) LIGHT SOURCE DEVICE FOR ENDOSCOPES

(75) Inventor: Shinya Matsumoto, Machida (JP)

(73) Assignee: Olympus Optical, Co., Ltd., Tokyo (JP)

( * ) Notice: Subject to any disclaimer, the term of this patent is extended or adjusted under 35 U.S.C. 154(b) by 0 days.

(21) Appl. No.: 09/870,469

(22) Filed: Jun. 1, 2001

(65) Prior Publication Data
US 2002/0123666 A1 Sep. 5, 2002

(30) Foreign Application Priority Data
Mar. 5, 2001 (JP) ........................ 2001-060556

(51) Int. Cl.[7] ............................................. A61B 1/00
(52) U.S. Cl. ................. 600/178; 600/180; 600/181; 600/160; 600/478; 359/385
(58) Field of Search ................... 600/178, 160, 600/181, 180, 184, 248, 476, 478; 359/385, 230, 234, 236, 228

(56) References Cited

U.S. PATENT DOCUMENTS

| | | | | |
|---|---|---|---|---|
| 4,569,334 A | * | 2/1986 | Ohshiro | 362/554 |
| 5,488,509 A | * | 1/1996 | Takahashi et al. | 359/385 |
| 5,675,689 A | * | 10/1997 | Nath | 385/125 |
| 5,823,943 A | | 10/1998 | Tomioka et al. | |
| 5,891,016 A | * | 4/1999 | Utsui et al. | 600/160 |
| 5,936,772 A | * | 8/1999 | Suzuki | 359/627 |
| 5,971,576 A | * | 10/1999 | Tomioka et al. | 362/268 |
| 5,993,037 A | | 11/1999 | Tomioka et al. | |
| 6,036,343 A | * | 3/2000 | Tomioka et al. | 362/268 |
| 6,076,932 A | * | 6/2000 | Uchida et al. | 359/585 |
| 6,086,531 A | | 7/2000 | Tomioka et al. | |
| 6,110,106 A | * | 8/2000 | MacKinnon et al. | 600/160 |
| 6,201,989 B1 | * | 3/2001 | Whitehead et al. | 250/461.2 |
| 6,231,503 B1 | * | 5/2001 | Sugimoto et al. | 362/574 |
| 6,293,911 B1 | * | 9/2001 | Imaizumi et al. | 600/160 |
| 6,465,968 B1 | * | 10/2002 | Sendai | 315/369.3 |

FOREIGN PATENT DOCUMENTS

| | | | | |
|---|---|---|---|---|
| JP | 8-106059 | 4/1996 | | |
| JP | 8-252218 | 10/1996 | | |
| JP | 2001281409 A | * | 10/2001 | A61B/1/00 |

OTHER PUBLICATIONS

Kevin T. Schomacker et al.; Lasers in Surgery and Medicine 12:63–78—Wiley–Liss, Inc., 1992.

* cited by examiner

Primary Examiner—Henry Bennett
Assistant Examiner—Kathryn Ferko
(74) Attorney, Agent, or Firm—Armstrong, Westerman & Hattori, LLP

(57) ABSTRACT

A light source device for endoscopes capable of preventing an incident end-face of a lightguide from generating heat due to infrared light emitted from a light source, and capable of radiating sufficient ultraviolet light and visible light. A light source emits at least ultraviolet light, visible light and infrared light. A condenser lens condenses the light emitted from the light source at the incident end-face of a light guide. A wavelength control filter and another selected filter are arranged between the light source and the condenser lens. Each optical axis of the light source, the wavelength control filter, the selected filter, the condenser lens, and the light-guide is linearly aligned, thereby providing a simplified alignment operation in manufacturing processes.

21 Claims, 8 Drawing Sheets

LIGHT SOURCE DEVICE FOR ENDOSCOPES

This invention claims benefit of Japanese Patent Application No. 2001-60556 filed on Mar. 5, 2001, the contents of which are incorporated by this reference.

FIELD OF THE INVENTION

The present invention relates to an endoscope system for observing fluorescent, and more particularly, to a light source device for irradiating an inspection object, or a subject, with an excitation light to induce fluorescence.

BACKGROUND OF THE INVENTION

Generally, by irradiating organic tissue with an excitation light, the organic tissue can be made to generate fluorescence having a longer wavelength than that of the excitation light. A fluorophor in the body includes collagen, NADH (nicotinamide adenine dinucleotide acid), FAD (flavin adenine dinucleotide), pilus zinc nucleotide, etc. The details are described in "Ultraviolet Laser-Induced Fluorescence of Colonic tissue" K. T. Schomacker et al., Lasers in Surgery and Medicine 12: 63–78 (1992).

In a combination of the phenomenon of generating fluorescence and fluorescence measuring techniques, tissue abnormality may be detected with high precision at a single cell level. Additionally, combining the fluorescence measuring techniques with endoscope techniques may provide a potential for diagnosing an early lesion which has been impossible to be detected by conventional endoscopes.

Connective tissue containing collagen resides substantially in the lower layer of mucosa, or submucosa. For example, when an endoscope transmits an excitation light from its lumen through the mucosa to excite the collagen, the fluorescence intensity to be induced is subject to the state, particularly the thickness, of the mucosa. Since cancer cells typically arise in the mucosa, the increased thickness of the mucosa caused by the grown cancer cells may attenuate the fluorescence. Thus, the position of the cancer cells may be identified to diagnose the lesion by measuring the attenuation of the fluorescence intensity. In this case, the collagen is typically excited by ultraviolet light or a blue component of visible light.

When the organic tissue is irradiated with ultraviolet light of 365 nm in wavelength, the organic tissue emits blue fluorescence having a peak at a wavelength of 460 nm due to NADH contained therein. The fluorescence intensity of NADH varies depending upon the oxidation-reduction state of NADH. In the tissue of low oxygen concentration, NAD (nicotinamide adenine dinucleotide) contained in the tissue is deoxidized and thereby the ratio of NADH is increased. Based on this, the fluorescence intensity of the tissue is increased.

Since the tissue of cancer cells, or cancerous tissue, is typically in an oxidation state, such tissue has a lower ratio of NADH and resultingly weaker fluorescence intensity. Thus, the cancerous tissue may be diagnosed by detecting this variance in the fluorescence intensity of NADH.

FIG. 13 shows a fluorescence spectrum of organic tissue irradiated with light of 365 nm in wavelength. As shown in FIG. 13, each fluorescence intensity of inflammatory tissue and cancerous tissue is lower than normal tissue. The same phenomenon will arise when organic tissue is irradiated with white light. FIG. 14 shows a reflection spectrum. As shown in FIG. 14, in a wavelength range of 400 to 600 nm, each reflection factor of inflammatory tissue and cancerous tissue is lower than normal tissue because the inflammatory tissue and cancerous tissue contain a larger amount of blood than that in the normal tissue. Japanese Patent Laid-Open Publication No. Hei 8-252218 discloses an endoscope adapted to selectively carry out visible light observation with the use of white light and fluorescent observation with the use of ultraviolet light by applying the above phenomenon.

Since fluorescent light, or fluorescence, detected by a fluorescent observation endoscope is weaker than the reflected light caused by irradiating with visible light, such fluorescent cannot be detected with a sufficient S/N ratio (signal—noise ratio) in regular endoscope observation. Thus, it is necessary to enhance the intensity of fluorescence to be detected. In order to improve this problem, it is effective to apply ultraviolet light of about 350 nm in wavelength to an excitation light. The conversion factor of the fluorescence resulting from exciting with the ultraviolet light is about ten times greater than that resulting from exciting with a blue component of visible light.

Conventional light source devices for endoscopes comprise a light source for emitting at least visible light between blue light and red light, an infrared cutoff filter for blocking infrared light, and a condenser lens for condensing light emitted from the light source at an incident end-face of a lightguide. The light emitted from the light source typically includes components of wavelengths other than that of visible light. Particularly, a xenon lamp may emit infrared light of 750 nm or more in wavelength with high energy. The light emitted from the light source is condensed at the incident end-face of the lightguide through the condenser lens. Then, light energy concentrated at the incident end-face of the lightguide is converted into thermal energy. The resultingly generated heat causes an undesirable high temperature at the incident end-face of the lightguide. In order to prevent this heat generation, the infrared cutoff filter is provided between the light source and the incident end-face of the lightguide to block infrared light. The infrared cutoff filter includes an infrared-cutoff interference filter composed of a transparent glass plate coated with a multilayer interference film and an infrared-cutoff absorption filter formed of a material capable of absorbing infrared light.

Japanese Patent Laid-Open Publication No. Hei 8-106059 discloses a method for dividing infrared light to block off the light in a particular frequency range. In this method, an interference filter and an absorption filter are disposed between a light source and an incident end-face of a lightguide. Spectral transmission factor properties of the infrared interference filter and infrared absorption filter are shown in the curves A and B of FIG. 15, respectively. Conventional infrared cutoff filters do not practically block light of 400 nm or less in wavelength and allow it to be transmitted therethrough. However, any transmission factor of an ultraviolet light region in the infrared interference filter is not specifically described. Further, as shown in FIG. 16, since the infrared interference filter has a sharp gradient of the transmission factor property around 350 nm in wavelength, the transmission factor in 350 nm in wavelength can be undesirably lowered to a large extent due to dispersion in manufacturing. In the interference filter, as compared with the transmission factor in the visible light region, the transmission factor in the ultraviolet light region is drastically lowered by a reflect action of the multilayer interference film and an absorption action of the material forming the multilayer interference film.

Thus, Japanese Patent Laid-Open Publication No. Hei 8-106059 merely discloses a technique for a regular light source optical system for endoscopes in which light of 400 nm or less in wavelength is not used and it is unnecessary to emit ultraviolet light, and describes a phenomenon that conventional infrared cutoff filters cannot sufficiently block light of about 400 nm in wavelength and resultingly allow it to be transmitted therethrough. However, when it is intended to positively emit ultraviolet light of 400 nm or less in wavelength (particularly, 350 nm in wavelength) with employing the infrared cutoff filter in a light source optical device for endoscopes, insufficient transmission factor of the ultraviolet light will be undesirably provided.

As described above, in the conventional infrared cutoff filters, ultraviolet light has a lower transmission factor than that of visible light. Consequently, when such infrared cutoff filters are applied to a light source for fluorescent observation endoscopes, ultraviolet light may not be sufficiently emitted.

SUMMARY OF THE INVENTION

In order to solve the aforementioned problems, it is an object of the present invention to provide a light source device for endoscopes capable of preventing an incident end-face of a lightguide from generating heat due to infrared light emitted from a light source, and capable of radiating sufficient ultraviolet light and visible light.

In order to achieve the above object, according to the present invention, there is provided a light source device for endoscopes for selectably applying fluorescent observation and reflection light observation with irradiation of blue to red visible light, said light source device comprising: a light source unit including a light source; a wavelength control filter; a condensing optics; and a lightguide, wherein the light source unit, the wavelength control filter, the condensing optics and the lightguide are linearly arranged along an optical axis, light from the light source unit includes at least light of ultraviolet wavelength and light of visible wavelength in the range of 400 to 650 nm and infrared wavelength when light from the light source unit is condensed at the light guide by the condensing optics, and the wavelength control filter is arranged between the light source and the lightguide, and the wavelength control filter transmits at least light of ultraviolet wavelength and visible light wavelength in the range of 400 to 650 and blocks light of infrared wavelength.

The objects of the present invention are also achieved by providing a light source device for endoscopes wherein the wavelength control filter satisfies the following conditions, $$T350 > 0.6 \tag{1}$$

$$T400\text{--}650 > 0.8 \tag{2}$$

$$T800\text{--}950 < 0.1 \tag{3}$$

where T350 is a transmission factor for 350 nm in wavelength, T400–650 is an average transmission factor for a wavelength range of 400 to 650 nm which is derived from averaging transmission factors measured in each 10 nm in a wavelength range of 400 to 650 nm, T800–950 is an average transmission factor for a wavelength range of 800 to 950 nm which is derived from averaging transmission factors measured in each 10 nm in a wavelength range of 800 to 950 nm.

The objects of the present invention are also achieved by providing a light source device for endoscopes wherein the wavelength control filter satisfies the following conditions, $$T350 > 0.8 \tag{4}$$

$$T400\text{--}650 > 0.8 \tag{2}$$

$$T800\text{--}950 < 0.1 \tag{3}$$

where T350 is a transmission factor for 350 nm in wavelength, T400–650 is an average transmission factor for a wavelength range of 400 to 650 nm which is derived from averaging transmission factors measured in each 10 nm in a wavelength range of 400 to 650 nm, T800–950 is an average transmission factor for a wavelength range of 800 to 950 nm which is derived from averaging transmission factors measured in each 10 nm in a wavelength range of 800 to 950 nm.

The objects of the present invention are also achieved by providing light source device for endoscopes wherein the wavelength control filter satisfies the following conditions, $$T350 > 0.6 \tag{1}$$

$$T400\text{--}650 > 0.8 \tag{2}$$

$$T800\text{--}1200 < 0.05 \tag{5}$$

where T350 is a transmission factor for 350 nm in wavelength, T400–650 is an average transmission factor for a wavelength range of 400 to 650 nm which is derived from averaging transmission factors measured in each 10 nm in a wavelength range of 400 to 650 nm, T800–1200 is an average transmission factor for a wavelength range of 800 to 1200 nm which is derived from averaging transmission factors measured in each 10 nm in a wavelength range of 800 to 1200 nm.

The objects of the present invention are also achieved by providing a light source device for endoscopes which further includes a means for blocking light of 330 nm or less in wavelength.

The objects of the present invention are also achieved by providing a light source device for endoscopes wherein the wavelength control filter is a transmission interference filter.

The objects of the present invention are also achieved by providing a light source device for endoscopes wherein the wavelength control filter includes a transmission interference filter and a transmission absorption filter.

The objects of the present invention are also achieved by providing a light source device for endoscopes wherein the wavelength control filter includes a transmission absorption filter and a transmission interference thin film provided on the surface of the transmission absorption filter.

The objects of the present invention are also achieved by providing a light source device for endoscopes, which further includes a color separating filter provided between the light source unit and the lightguide.

The objects of the present invention are also achieved by providing a light source device for endoscopes wherein the wavelength control filter includes three or more reflection surfaces, and is adapted to inflect the optical axis therein.

The objects of the present invention are also achieved by providing a light source device for endoscopes wherein the wavelength control filter is a reflection interference filter.

The objects of the present invention are also achieved by providing a light source device for endoscopes wherein the wavelength control filter includes a reflection interference filter and a transmission absorption filter.

The objects of the present invention are also achieved by providing a light source device for endoscopes wherein the wavelength control filter includes a reflection interference filter and a transmission interference filter.

The objects of the present invention are also achieved by providing a light source device for endoscopes wherein the single light source includes a light emission part and a reflector.

The objects of the present invention are also achieved by providing a light source device for endoscopes wherein the reflector has an ellipse shape.

The objects of the present invention are also achieved by providing a light source device for endoscopes wherein the reflector has a parabola shape.

The objects of the present invention are also achieved by providing a light source device for endoscopes wherein the light guide has an incident end-face, wherein the incident end-face is adjustably located at a position where ultraviolet light is condenses by the condensing optics.

The objects of the present invention are also achieved by providing a light source device for endoscopes wherein the light guide has an incident end-face, wherein when the transmission interference filter is arranged along the optical axis to allow fluorescent observation to be conducted, the incident end-face of the lightguide is adjustably located at a position where ultraviolet light is condenses by the condensing optics, and when the transmission interference filter is spaced apart from the optical axis to allow visible light observation to be conducted, the incident end-face of the lightguide is adjustably located at a position where visible light is condenses by the condensing optics.

The objects of the present invention are also achieved by providing a light source device for endoscopes wherein the wavelength control filter is an interference filter including an amorphous thin film.

The objects of the present invention are also achieved by providing a light source device for endoscopes wherein the interference filter is formed by laminating at least two groups of the amorphous thin films, wherein one group of the amorphous thin film has a high refractive index and includes at least one component selected from the group consisting of $Sc_2O_5$, $Ta_2O_5$, $HfO_2$ and $ZrO_2$, and another group of the amorphous thin film has a low refractive index and included at least one component selected from the group consisting of $SiO_2$ and $MgF_2$.

Other features and advantages of the present invention will be apparent from the accompanying drawings and from the detailed description.

DESCRIPTION OF THE PREFERRED EMBODIMENT

Figure 1:
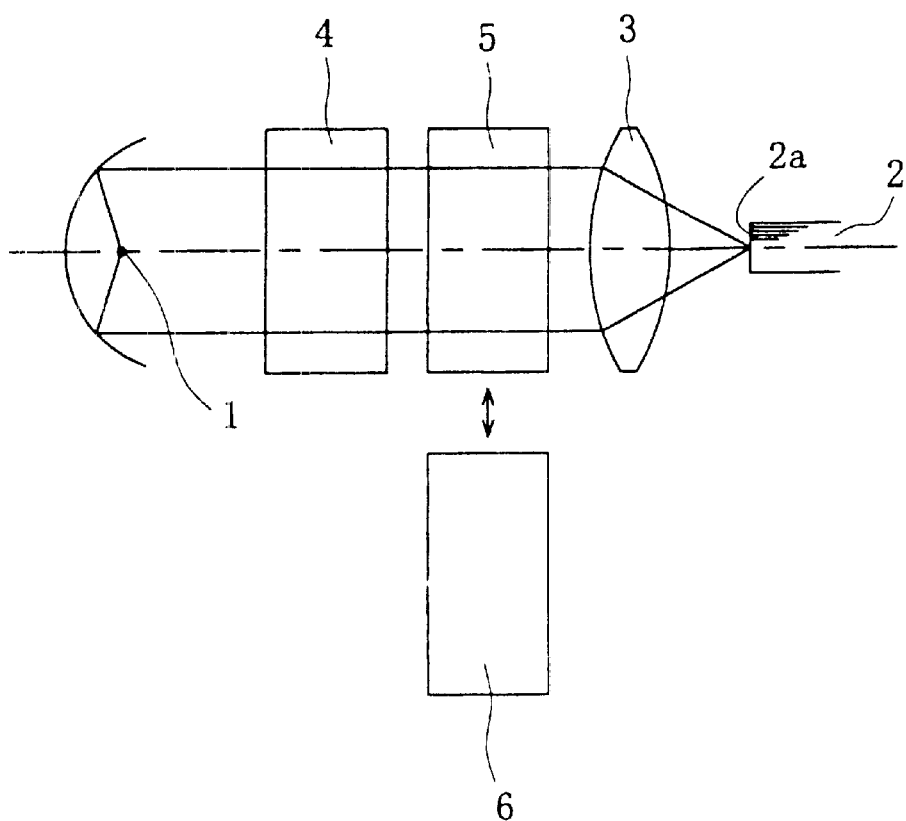
FIG. 1 is a sectional view showing a light source device for endoscopes according to a first embodiment of the present invention.

With reference to the drawings, various embodiments of the present invention will now be described. In each embodiment, the same elements of structure are defined by the same reference numerals, and their details will be described only in a first embodiment and will be omitted in other embodiments.

First Embodiment

FIG. 1 is a sectional view showing a light source device for endoscopes according to a first embodiment of the present invention. As shown in FIG. 1, the reference numeral 1 designates a light source. Specifically, the light source may comprise a xenon lamp, metal halide lamp, extra high-pressure mercury lamp or the like. The light source emits at least ultraviolet light, visible light and infrared light. The reference numeral 2 designates a lightguide having an incident end-face 2a. The reference numeral 3 designates a condenser lens. The condenser lens serves as a condensing optics for condensing light emitted from the light source 1 at the incident end-face 2a of the light guide 2. A wavelength control filter 4 and either filter 5 or filter 6 are arranged between the light source 1 and the condenser lens 3. The light source device is adapted to selectably interchange filter 5 and 6. In turn from the side of the light source 1 toward the incident end-face 2a of the lightguide 2, the wavelength control filter 4, either one of the filters 5 and 6; and the condenser lens 3 are arranged. In the first embodiment, each optical axis of the light source 1, the wavelength control filter 4, either one of the filters 5 and 6, the condenser lens 3, and the lightguide 2 is linearly aligned. This provides a simplified alignment operation in manufacturing processes.

Figure 2:
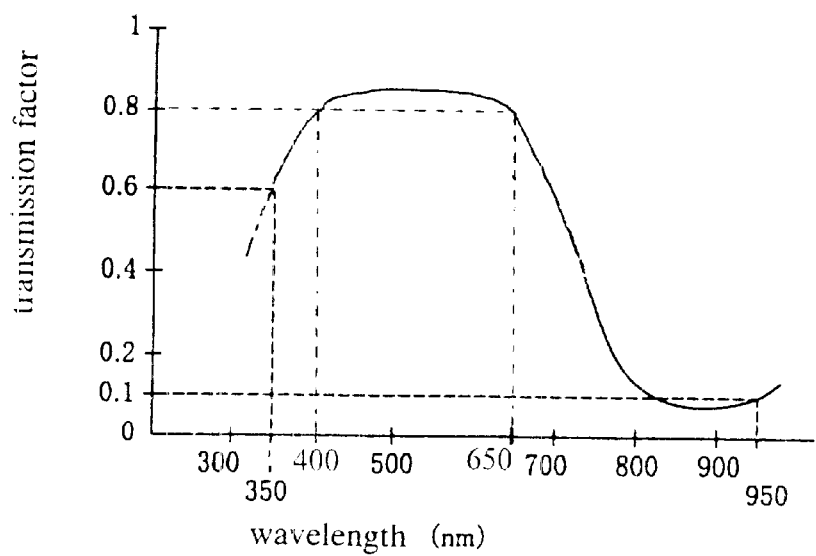
FIG. 2 is a diagram showing a spectral transmission factor property of a wavelength control filter used in the first embodiment of the present invention.

FIG. 2 shows a spectral transmission factor property of the wavelength control filter 4. The wavelength control filter 4 satisfies the following conditional expressions (1), (2) and (3). In the conditional expressions, T350 indicates a transmission factor for 350 nm in wavelength. T400–650 indicates an average transmission factor for a wavelength range of 400 to 650 nm, and this average transmission factor is a value derived from averaging transmission factors measured in each 10 nm in a wavelength range of 400 to 650 nm. T800–950 indicates an average transmission factor for a wavelength range of 800 to 950 nm, and this average transmission factor is a value derived from averaging transmission factors measured in each 10 nm in a wavelength range of 800 to 950 nm.

$$T350 > 0.6 \tag{1}$$

$$T400\text{--}650 > 0.8 \tag{2}$$

$$T800\text{--}950 < 0.1 \tag{3}$$

The filter 5 transmits light in a wavelength range of 350 to 400 nm, but blocks light in a wavelength range of 400 to 800 nm. Since the wavelength control filter 4 satisfies the conditional expression (1), the light source device may irradiate a subject region with ultraviolet light including 350 nm in wavelength.

The light source device may emit only ultraviolet light by arranging the filter 5 in an optical path of the light source device. Thus, NADH contained in the subject region is excited by the ultraviolet light, and the induced fluorescence may be observed.

The filter 6 transmits light of all or part of a wavelength range of 400 to 650 nm. Thus, in view of only wavelength property, the filter 6 is not essentially necessary, and a similar effect may be obtained by removing the filter 5 out of the optical path. However, in order to allow the condensing means 3 to condense light at a constant position, it is desirable to insert the filter 6 having the same thickness as that of the filter 5 to provide the same optical path length when the filter 5 is removed.

The wavelength control filter 4 satisfies the conditional expression (2) for visible light in a wavelength range of 400 to 650 nm. The light source device may emit visible light of blue to red components by arranging another filter 6 in the optical path, and regular endoscope observation may also be carried out by irradiating with visible light. Thus, according to this embodiment, visible light observation may be carried out in conjunction with fluorescent observation, and an adequate diagnosis may be conducted with mutually consulting these observations.

The wavelength control filter 4 also satisfies the conditional expression (3) for infrared light of a wavelength range of 800 to 950 nm. This infrared light is disadvantageous to the light source device for endoscopes because the infrared light causes an undesirable heat generation at the incident end-face 2a of the lightguide 2. Since the wavelength control filter 4 prevents 90% or more energy of the infrared light from being transmitted to the side of the incident end-face 2a of the lightguide 2, the heat generation in the incident end-face 2a may be appropriately restrained.

Second Embodiment

Figure 3:
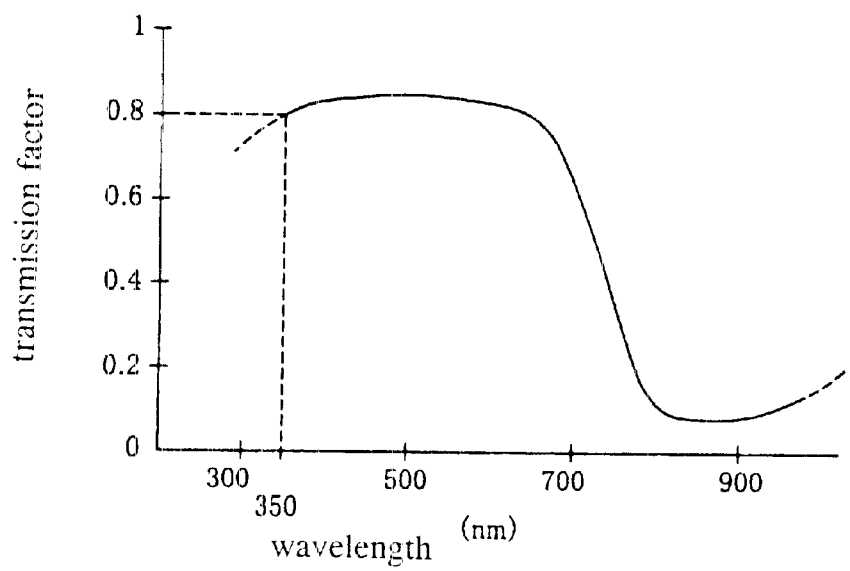
FIG. 3 is a diagram showing a spectral transmission factor property of a wavelength control filter used in a second embodiment of the present invention.

FIG. 3 shows a spectral transmission factor property of a wavelength control filter 4 used in a second embodiment. The structure of the optical system of this embodiment is the same as that of the first embodiment.

Generally, fluorescence detected by a fluorescent observation endoscope is weak. Thus, in order to enhance the intensity of fluorescence to be detected, it is necessary to increase output of the light source. This results in undesirably enlarged size and increased cost of the light source. In this regard, it is effective to increase the transmission factor of ultraviolet light in the wavelength control filter 4. As in the first embodiment, the wavelength control filter 4 also satisfies the conditional expressions (2) and (3).

The wavelength control filter 4 satisfies the following conditional expression (4). In the conditional expressions, T350 indicates a transmission factor of the wavelength control filter 4 for 350 nm in wavelength.

$$T350 > 0.8 \tag{4}$$

Since the wavelength control filter 4 satisfies the conditional expression (4), the light source device may irradiate a subject region with ultraviolet light including 350 nm in wavelength.

Further, the light source device may emit only ultraviolet light by arranging the filter 5 in the optical path. Thus, NADH contained in the subject region is excited by the ultraviolet light, and the induced fluorescence may be observed.

Third Embodiment

Figure 4:
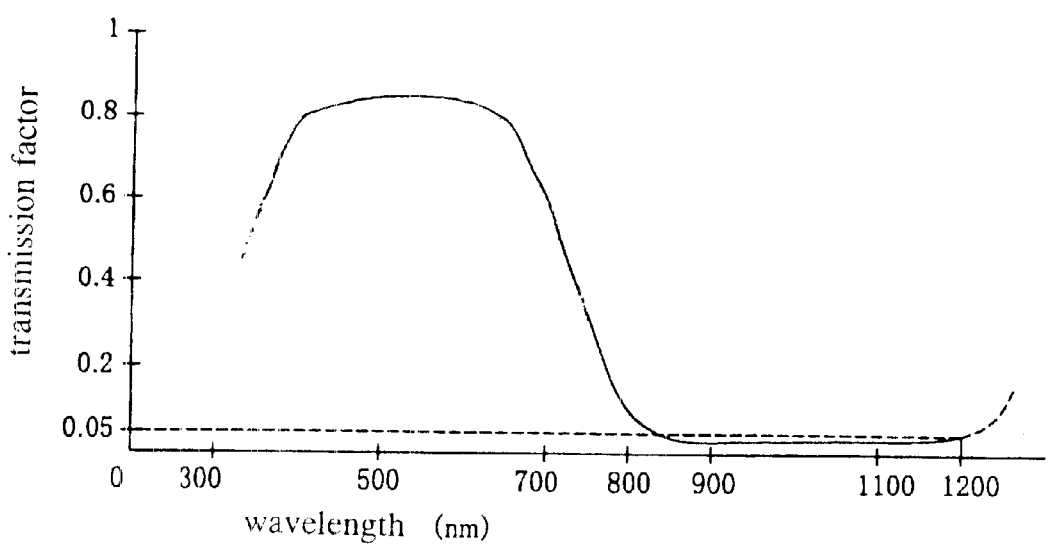
FIG. 4 is a diagram showing a spectral transmission factor property of a wavelength control filter used in a third embodiment of the present invention.

FIG. 4 shows a spectral transmission factor property of a wavelength control filter 4 used in a third embodiment. The structure of the optical system of the third embodiment is the same as that of the first embodiment.

In particular, when a xenon lamp or halogen lamp is applied to the light source 1, higher thermal energy is undesirably condensed at the incident end-face 2a of the lightguide 2 due to greater infrared light component included in such a light source. Thus, it is desirable to prevent the infrared light component emitted from the light source 1 from entering into the incident end-face 2a of the lightguide 2 by use of the wavelength control filter 4 as in this embodiment.

The wavelength control filter 4 satisfies the following conditional expression (5). In the conditional expressions, T800–1200 indicates an average transmission factor for a wavelength range of 800 to 1200 nm, and this average transmission factor is a value derived from averaging transmission factors measured in each 10 nm in a wavelength range of 800 to 1200 nm.

$$T800-1200 < 0.05 \tag{5}$$

As in the first embodiment, the wavelength control filter 4 also satisfies the conditional expressions (1) and (2). Since the wavelength control filter 4 prevents 95% or more energy of the infrared light from being transmitted to the side of the incident end-face 2a of the lightguide 2, the heat generation in the incident end-face 2a may be significantly restrained.

Generally, each wavelength control filter 4 in the aforementioned first to third embodiments comprises an interference filter. The interference filter includes a transmission interference filter and a reflection interference filter. The transmission interference filter reflects infrared rays and transmits light in a necessary wavelength band other than infrared rays. The reflection interference filter transmits infrared rays and reflects light in a necessary wavelength band other than infrared rays.

In order to obtain further reduced quantity of transmission light, each wavelength control filter 4 in the aforementioned first to third embodiments is constructed by combining the transmission interference filter with the transmission absorption filter. Otherwise, the transmission interference filter may be formed on the surface of the transmission absorption filter. When the light source emits infrared light, the wavelength control filter 4 is required to prevent the heat generation in the incident end-face 2a of the lightguide 2.

However, when the transmission absorption filter is used by itself or arranged proximate to the light source, the heat generation cased by infrared rays absorbed in a glass plate of the transmission absorption filter can provide unallowable thermal expansion in the glass plate, resulting in breakdown of the glass. Thus, when the transmission absorption filter is applied with the transmission interference filter, it is necessary to arrange the transmission interference filter at a position closer to the light source than that of the transmission absorption filter.

Fourth Embodiment

Figure 5:
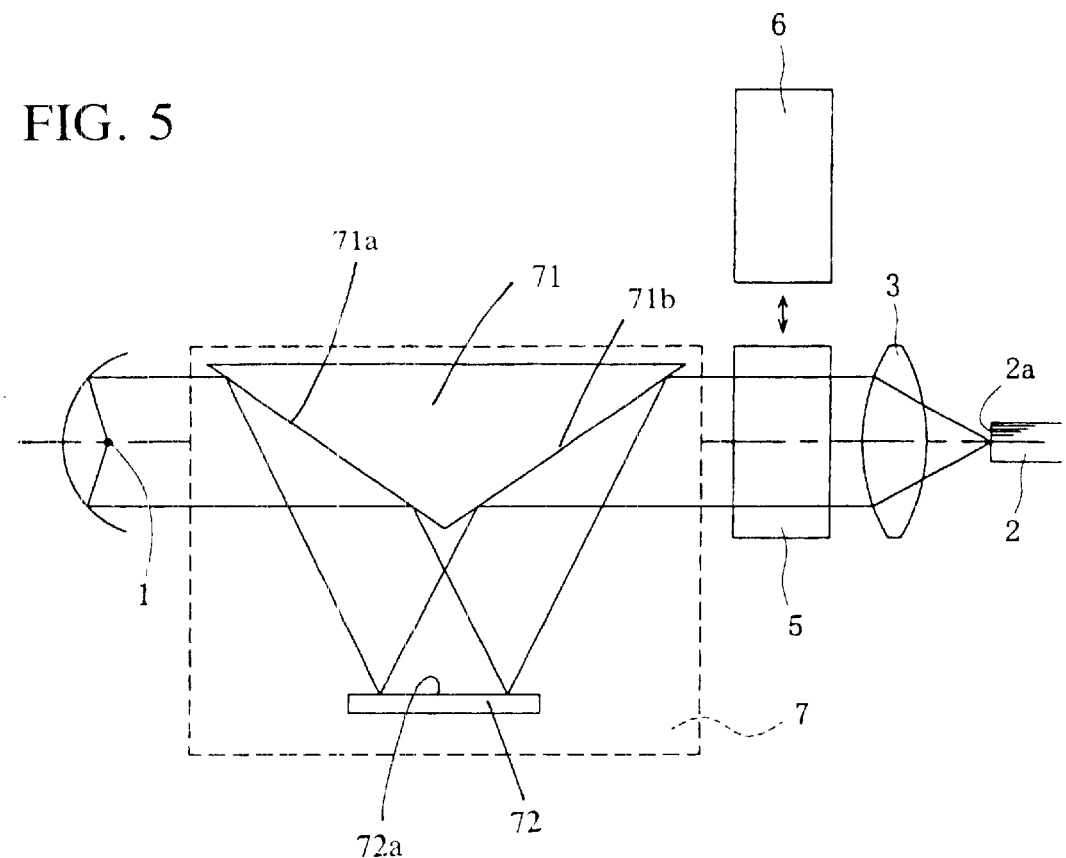
FIG. 5 is a sectional view showing a light source device for endoscopes according to a fourth embodiment of the present invention.

FIG. 5 is a sectional view showing a light source device for endoscopes according to a fourth embodiment.

In the forth embodiment, in turn from the side of the light source 1 toward the incident end-face 2a of the lightguide 2, a reflection interference filter 7 comprised of a triangular prism 71 with reflecting surfaces 71a, 71b and a plate 72 with a reflecting surface 72a, either one of the filters 5 and 6 and a condenser lens 3 are arranged. The reflection interference filter 7 has either one of the spectral transmission factor properties shown in FIGS. 2, 3 and 4. That is, reflection factor is substituted for transmission factor in each figure. The reflection interference filter 7 satisfies one of the following combinations of the conditional expressions;

conditional expressions (1) (2) (3)

conditional expressions (4) (2) (3)

conditional expressions (1) (2) (5)

where reflection factor is substituted for transmission factor in each expression.

The filter 5 transmits light in a wavelength range of 350 to 400 nm, but blocks light in a wavelength range of 400 to 800 nm. The reflection interference filter 7 has 3 or more reflection surfaces. The reflection interference filter 7 may be combined with a transmission absorption filter or transmission interference filter.

Preferably, each interference filter used in the first to fourth embodiments is an amorphous thin film. The term "amorphous" means that atomic arrangement is not formed in a crystal structure and in an unregulated noncrystal state. A vapor deposition process with ion plating or ion assist is suitable for manufacturing the amorphous thin film. This vapor deposition process may provide a thin film uniformly formed in the direction of the optical axis and the direction orthogonal thereto, and the resulting thin film serving as the interference filter may obtain the spectral transmission factor or spectral reflection factor shown in FIGS. 2, 3 or 4.

Each interference filter used in the first to fourth embodiments is composed of laminated layers of a high refractive index thin layer and a low refractive index layer, which have no absorption at least in a wavelength range of 350 nm or more. The high refractive index thin layer means a thin layer having a refractive index of 1.7 or more in a visible wavelength range. The low refractive index thin layer means a thin layer having a refractive index of 1.5 or less in a visible wavelength range. As the difference in refractive index between the high refractive index thin layer and the low refractive index layer becomes lager, the interference filter may have more improved performance with less number of layers. Thus, it is desirable to have a large difference in respective refractive indices of these two thin films. Preferably, the refractive index of the high refractive index thin layer is 1.9 or more.

In each interference filter used in the first to fourth embodiments, the high refractive index thin layer includes either one of $Sc_2O_5$, $Ta_2O_5$, $HfO_2$ and $ZrO_2$ as a primary component. The low refractive index thin layer includes either one of $SiO_2$ and $MgF_2$ as a primary component. Among the aforementioned components for the high refractive index thin layer, $Ta_2O_5$ is particularly preferable because it may facilitate the production of a precision thin film.

In each transmission interference filter used in the first to fourth embodiments, when it is intended to have a design frequency $\lambda$ in the range of 750 to 1000 nm, the thin film composed of laminated layers of the high refractive index thin layer and the low refractive index layer is preferably provided by repeatedly laminating a high refractive index thin layer having a optical thin layer in the range of 0.24 $\lambda$ to 0.26 $\lambda$ and a low refractive index layer having a optical thin layer of 0.25 $\lambda$. The resulting thin film serving as the transmission interference filter may obtain the spectral transmission factor shown in FIGS. 2, 3 or 4.

Fifth Embodiment

Figure 6:
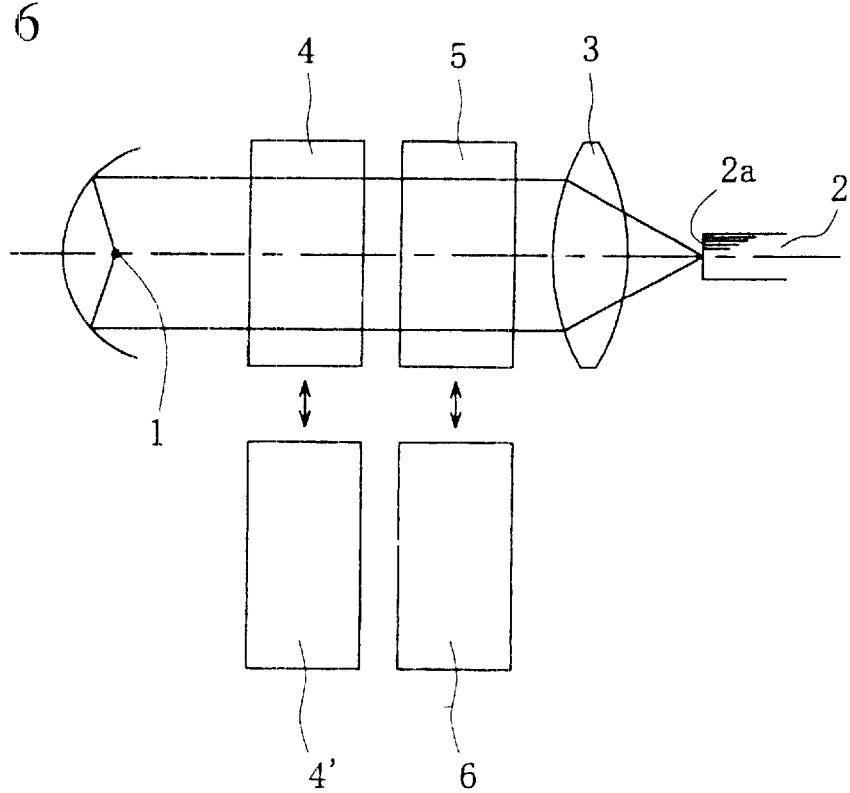
FIG. 6 is a sectional view showing a light source device for endoscopes according to a fifth embodiment of the present invention.

FIG. 6 is a sectional view showing a light source device for endoscopes according to a fifth embodiment. In the fifth embodiment, between the light source 1 and the condenser lens 3, either one of the wavelength control filter 4 and an additional wavelength control filter 4', and either one of the filters 5 and 6 are selectably arranged, respectively. The wavelength control filter 4 has either one of the spectral properties shown in FIGS. 2, 3 and 4, where the vertical axis in each figure indicates spectral transmission factor for the transmission interference filter, and spectral reflection factor for the reflection interference filter. The additional wavelength control filter 4' has another spectral property different from that of the wavelength control filter 4. The spectral property of the additional wavelength control filter 4' is, for example, shown in FIGS. 2, 3, 4, or 7. The filter 5 transmits light in a wavelength range of 350 to 400 nm, but blocks light in a wavelength range of 400 to 800 nm.

When the wavelength control filter 4 and the filter 5 is arranged in the optical path, fluorescent observation with ultraviolet light becomes possible. Further, when the additional wavelength control filter 4' and the filter 6 are arranged in the optical path, the spectral property of light condensed at the incidence end-face 2a of the lightguide 2 may be varied. This makes it possible to conduct, for example, regular observation with visible light, (non-medical) fluorescent observation, medical fluorescent observation, infrared observation, etc.

The wavelength control filter 4 satisfies the conditional expression (2). Thus, by selectively arranging either one of the filters 5 and 6 in the optical path, a combinational observation of fluorescent observation with ultraviolet light and the reflected light caused by irradiating with visible light of certain visible wavelength may be selectably conducted, and fluorescent observation with ultraviolet light may be switched to regular observation, medical fluorescent observation, etc.

Figure 7:
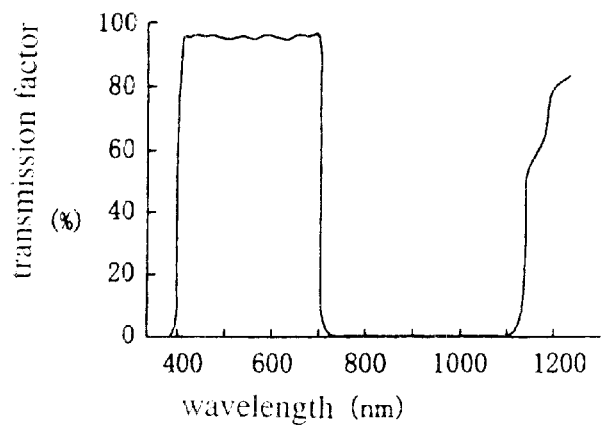
FIG. 7 is a diagram showing a spectral transmission factor property of an additional wavelength control filter different from a wavelength control filter 4 shown in FIG. 6.

When the spectral property shown in FIG. 7 is applied to the additional wavelength control filter 4' and the filter 6 is selectively arranged in the optical path, regular observation with visible light, (non-medical) fluorescent observation and medical fluorescent observation may be selectably conducted.

During the observation by irradiating with visible light, undesirable light of 400 nm or less and 800 nm or more in wavelength is not condensed at the incident end-face 2a of the lightguide 2. This desirably prevents the incident end-face 2a from generating heat.

Sixth Embodiment

Figure 8:
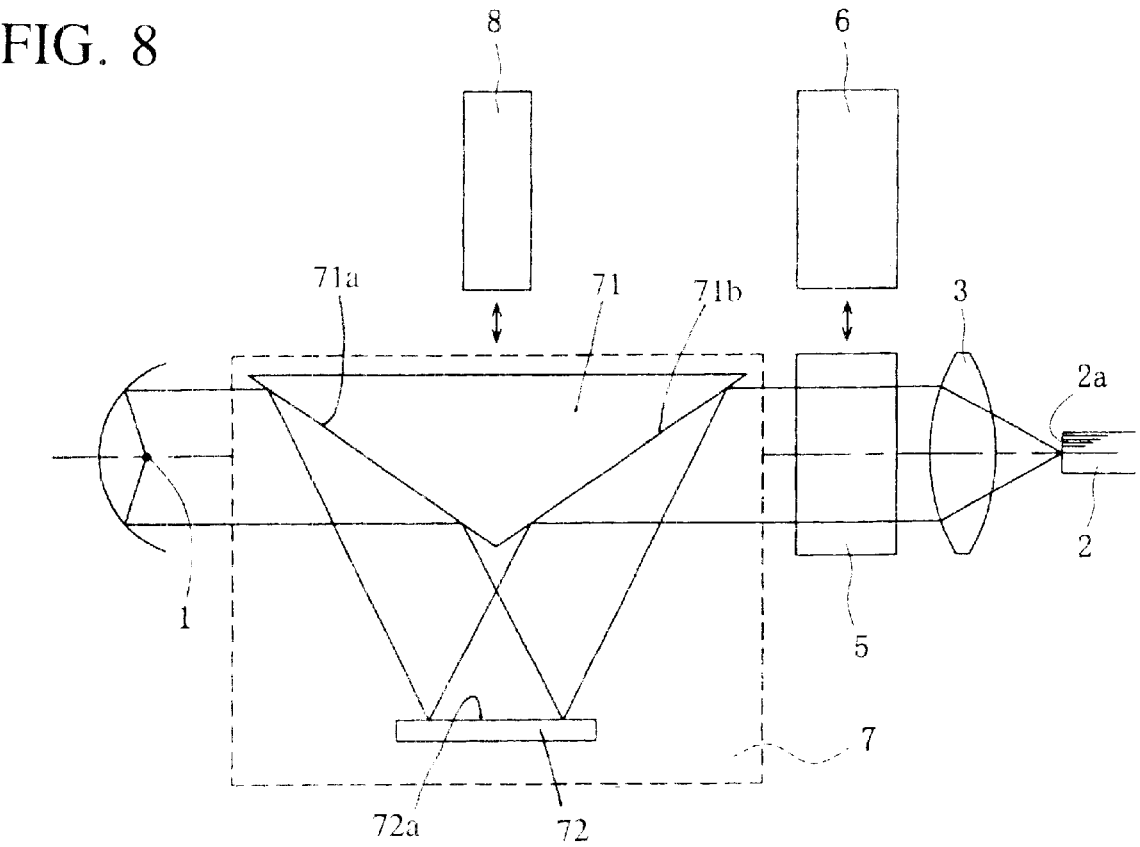
FIG. 8 is a sectional view showing a light source device for endoscopes according to a sixth embodiment of the present invention.

FIG. 8 is a sectional view showing a light source device for endoscopes according to a sixth embodiment. In the sixth embodiment, between the light source 1 and the condenser lens 3, either one of the reflection interference filter 7 and a transmission interference filter 8, and either one of the filters 5 and 6 are selectably arranged, respectively. In this case, the physical relationship between the light source 1 and the incident end-face 2a of the lightguide 2 is not varied. The reflection interference filter 7 has either one of the spectral reflection factor properties shown in FIGS. 2, 3 and 4. The transmission interference filter 8 has either one of the spectral properties shown in FIGS. 2, 3, 4 and 7. However, the spectral property of the reflection interference filter 7 is selected differently from that of the transmission interference filter 8.

In the transmission interference filter 8, an incident optical axis and outgoing optical axis are in parallel with each other. It is necessary to parallelize an incident optical axis to the reflection interference filter 7 and an outgoing optical axis therefrom in order to make it possible to change the reflection interference filter 7 and transmission interference filter 8 each other. As shown in FIG. 8, since the reflection interference filter 7 is configured to have three reflection surfaces, the parallelized optical axes may be readily provided. The reflection interference filter may have more than three reflective surfaces.

Seventh Embodiment

Figure 9:
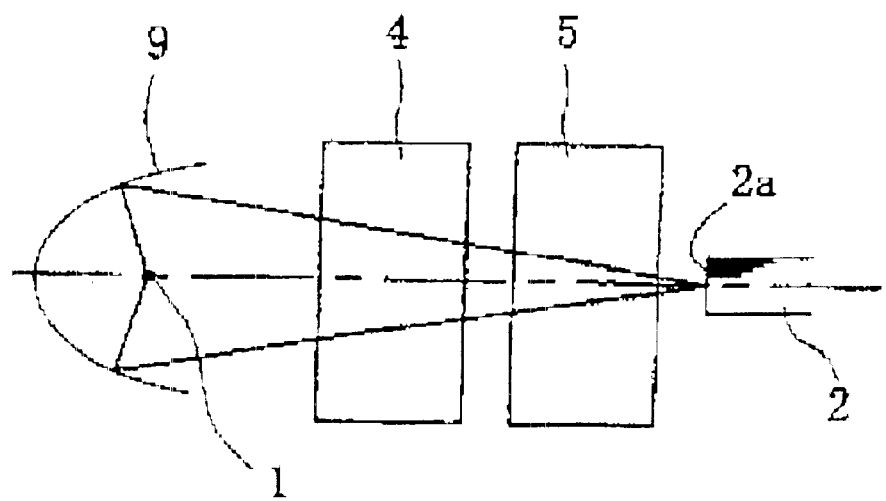
FIG. 9 is a sectional view showing a light source device for endoscopes according to a seventh embodiment of the present invention.

FIG. 9 is a sectional view showing a light source device for endoscopes according to a seventh embodiment. In the seventh embodiment, an elliptical reflector 9 is applied to the condensing means to condense light emitted from the light source 1 at the incident end-face 2*a* of the lightguide 2. Applying the elliptical reflector 9 to the condensing means allows the condenser lens 3 to be eliminated. Thus, the optical system may be simplified. Further, the number of optical surfaces may be reduced and thereby light-quantity loss caused by reflection and scattering at the optical surfaces may be desirably lowered.

On the other hand, when the condenser lens 3 is arranged in the optical path between the light source 1 and the incident end-face 2*a* of the lightguide 2 in addition to the elliptical reflector 9, an improved performance of condensing light at the incident end-face 2*a* is desirably provided.

Eighth embodiment

Figure 10:
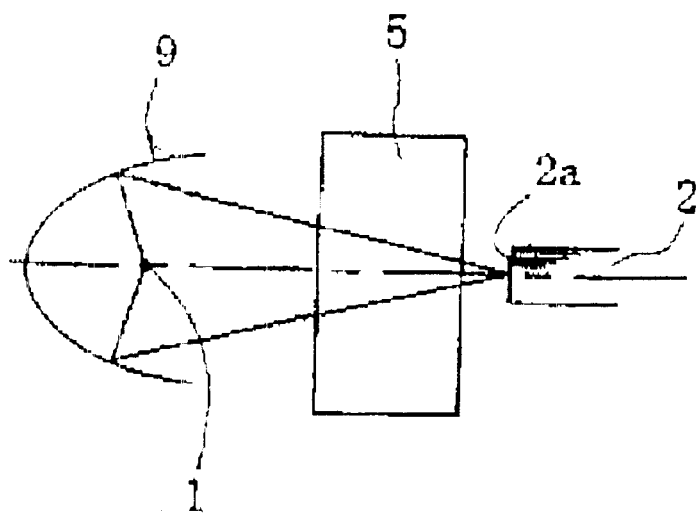
FIG. 10 is a sectional view showing a light source device for endoscopes according to an eighth embodiment of the present invention.

FIG. 10 is a sectional view showing a light source device for endoscopes according to an eighth embodiment. In the eighth embodiment, by providing the elliptical reflector 9 having a function of the reflection interference filter, the wavelength control filter 4 is eliminated. The elliptical reflector 9 has either one of the spectral reflection factor properties shown in FIGS. 2, 3 and 4. Thus, when the elliptical reflector 9 is adapted to function as the reflection interference filter, the optical system may be simplified. Further, the number of optical surfaces may be reduced and thereby light-quantity loss caused by reflection and scattering at the optical surfaces may be desirably lowered.

Furthermore, a parabolic reflector may substitute for the elliptical reflector 9. In this case, the parabolic reflector may be adapted to function as the reflection interference filter.

Since the elliptical reflector 9 or the parabolic reflector serves as the wavelength control filter 4, the function of the wavelength control filter may be dispersed to a plurality of optical surfaces. This allows the performance required for each optical surface to be reasonably lowered. As a result, the light source device may be readily produced, and may obtain a highly improved function of the wavelength control filter as a whole.

Ninth Embodiment

Figure 11:
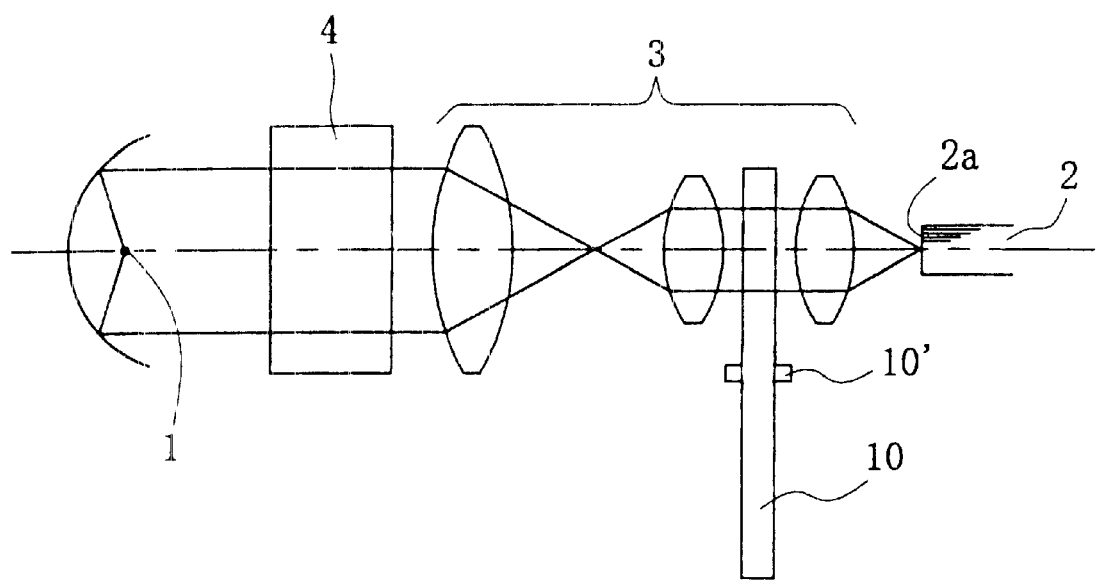
FIG. 11 is a sectional view showing a light source device for endoscopes according to a ninth embodiment of the present invention.

FIG. 11 is a sectional view showing a light source device for endoscopes according to a ninth embodiment. In the ninth embodiment, in turn from the side of the light source 1, the wavelength control filter 4 and the condenser lens 3 are arranged between the light source 1 and the incident end-face of the lightguide 2. A color separating filter 10 is arranged at a position where light flux is parallelized by the condenser lens 3. The wavelength control filter 4 has either one of the spectral transmission factor properties shown in FIGS. 2, 3 and 4.

Figure 12:
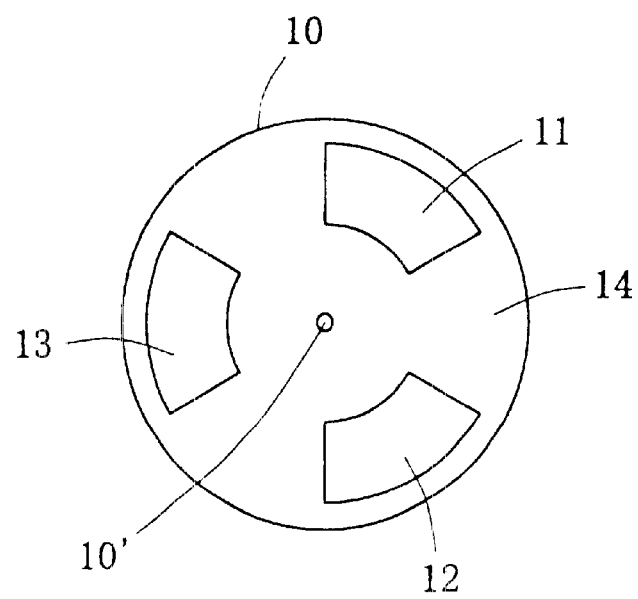
FIG. 12 is a front view of a color separating filter used in the ninth embodiment.
Figure 13:
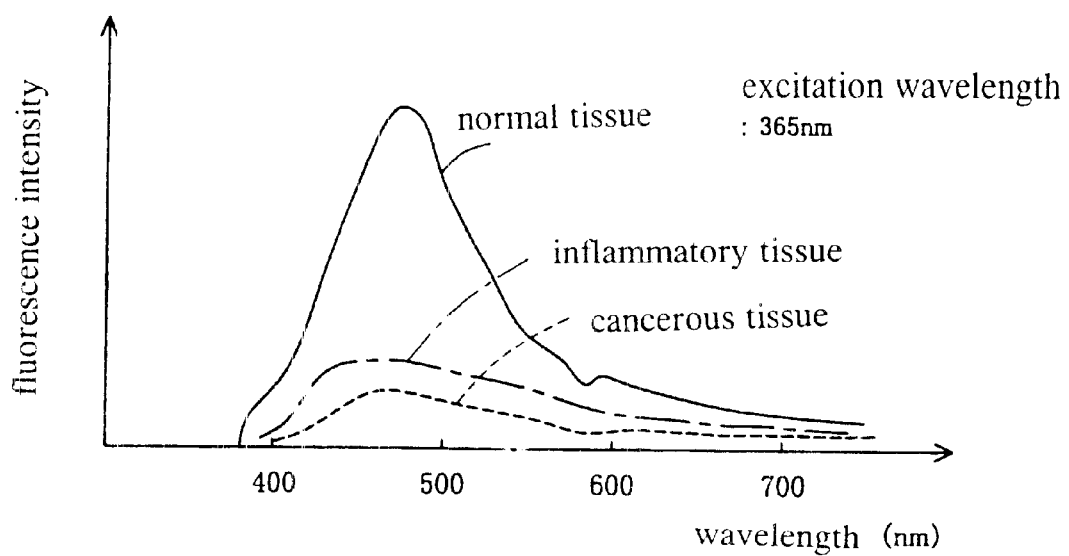
FIG. 13 is a diagram showing a fluorescence spectrum of organic tissue irradiated with light of 365 nm in wavelength.
Figure 14:
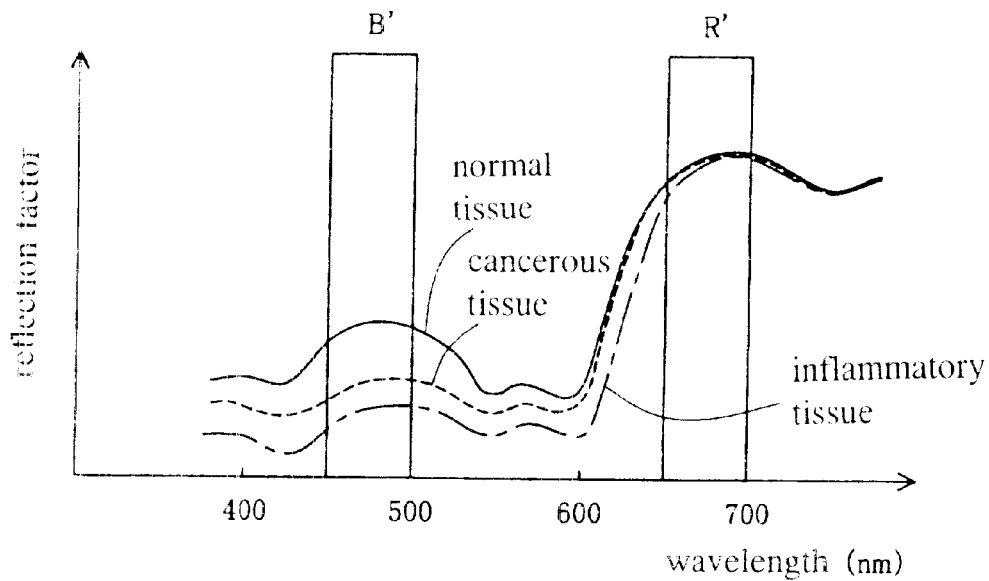
FIG. 14 is a diagram showing a degraded state in each reflection factor of inflammatory tissue and cancerous tissue in a wavelength range of 400 to 600 nm.
Figure 15:
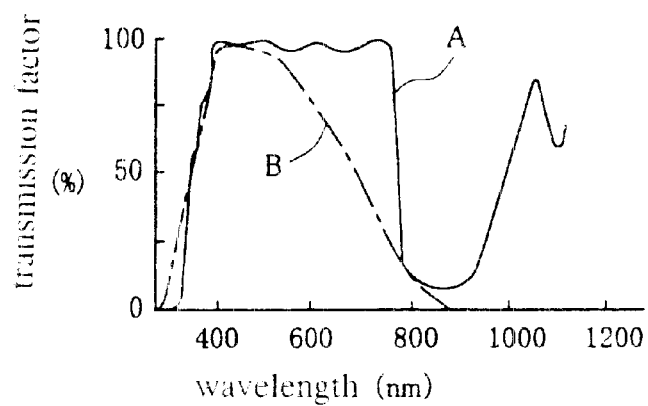
FIG. 15 is a diagram showing spectral transmission factor properties of a conventional infrared-cutoff interference filter and infrared-cutoff absorption filter.

FIG. 12 is a front view of the color separating filter 10, viewing along the optical axis. The color separating filter 10 is adapted to rotate about a shaft 10' parallel with the optical axis. The color separating filter 10 is provided with different kinds of band-pass filters 11, 12, and 13 and a light blocking section 14 which are sequentially interposed in the optical path according to the rotation of the color separating filter 10. Light passing through one of the band-pass filters intermittently irradiates an inspection object through the lightguide 2. The band-pass filter 11 transmits light only in a wavelength range of about 350 to 400 nm. The band-pass filter 12 transmits light only in a wavelength range of about 400 to 450 nm. The band-pass filter 13 transmits light only in a wavelength range of about 600 to 650 nm. In combination of organic autofluorescence caused by irradiating with light in a wavelength range of 350 to 400 nm and the reflected light (scattered light) caused by irradiating with light in a wavelength range of 400 to 450 nm and in a wavelength range of 600 to 650 nm, various observations may be conducted. The spectral transmission factor of each band-pass filter 11, 12, 13 may be modified according to purposes.

In the first to ninth embodiments, when the emitted light from the light source is condensed at the incident end-face 2*a* of the lightguide 2, an optimum spot position where the light is condensed into a smallest area by the condenser lens exists in the direction of the optical axis. Thus, the irradiation intensity of ultraviolet light may be enhanced by matching the position of the incident end-face 2*a* in the direction of the optical axis with the optimum spot position.

Generally, ultraviolet light and visible light have different optimum spot positions, respectively, depending on the positional distribution of the spectral emission property of the light source 1, the chromatic aberration of the condenser lens 3, etc. Fluorescence caused by irradiating with ultraviolet light is weaker than the reflected light (scattered light) detected in regular observation. Thus, when the combined observation of fluorescence caused by irradiating with ultraviolet light and the reflected light (scattered light) caused by irradiating with visible light is conducted in the same endoscope observation system, the fluorescent observation has an inferior S/N ratio. Therefore, even if the irradiation intensity of visible light is lowered, the irradiation intensity of ultraviolet light may be enhanced by matching the incident end-face 2*a* of the lightguide 2 with the optimum spot position of ultraviolet light, and thereby fluorescence intensity may also be enhanced. Consequently, the endoscope observation system may have an improved S/N ratio as a whole.

In the first to ninth embodiments, when a fluorescent observation mode adapted to irradiate with ultraviolet light and a visible light observation mode adapted to irradiate with visible light are switched each other, the position of the incident end-face 2*a* of the lightguide 2 may be moved in sync with the switching operation.

In the fluorescent observation, the position of the incident end-face 2*a* of the lightguide 2 in the direction of the optical axis may be matched with the optimum spot position of ultraviolet light. Specifically, when the condensing optics is composed of a positive lens, the optimum spot position of ultraviolet light is located closer to the side of the positive lens (the side of light source) than the optimum spot position of visible light. When the condensing optics is composed of a reflector and a negative lens, the optimum spot position of ultraviolet light is located closer to the side of the lightguide (the side of an inspection object) than the optimum spot position of visible light.

In the visible observation adapted to irradiate with visible light, the position of the incident end-face 2a of the lightguide 2 in the direction of the optical axis may be matched with the optimum spot position of visible light. Specifically, when the condensing optics is composed of a positive lens, the optimum spot position of visible light is located closer to the side of the lightguide (the side of an inspection object) than the optimum spot position of ultraviolet light. When the condensing optics is composed of a reflector and a negative lens, the optimum spot position of visible light is located closer to the side of the negative lens (the side of light source) than the optimum spot position of ultraviolet light.

In the visible observation, it is occasionally necessary to equalize both intensities of the reflected light (scattered light) and fluorescence caused by irradiating with ultraviolet light in consideration of a dynamic range of an imaging element. In this case, the position of the incident end-face 2a of the lightguide 2 in the direction of the optical axis may be shifted from the optimum spot position of visible light for the visible observation mode to lower the irradiation intensity of visible light. As another approach for lowering the irradiation intensity of visible light, the position of the incident end-face 2a of the lightguide 2 may be shifted in the direction perpendicular to the optical axis.

In the first to ninth embodiment, the light source comprises a reflector and a cover glass. The light source is preferable not to emit light of 330 nm or less in wavelength. However, when a xenon lamp, metal halide lamp, extra high-pressure mercury lamp or the like is applied to the light source, light of 330 nm or less in wavelength will be emitted from the light source. Thus, it is necessary to block light of 330 nm or less in wavelength by the components of the light source, such as the reflector or cover glass. The interference filter is used for blocking light of 330 nm or less.

When light of 330 nm or less in wavelength is not emitted, ozone caused by ultraviolet light is never generated. This is advantageous to avoid corrosion of metal parts in the light source device.

Further, when ultraviolet light is transmitted through the optical system, optical materials are colored due to solarization. It is important to select a material having a sufficient resistance against solarization for the optical materials of the optical system. However, the shorter wavelength of ultraviolet light, the higher potentiality of solarization. Thus, it is desirable not to transmit unnecessary ultraviolet light through the optical system.

In fluorescent observation, given that fluorophor is NADH, the peak value of the irradiation efficiency for NADH is yielded by light of about 365 nm in wavelength. This means that light of 330 nm in wavelength is unnecessary and is desirable to be blocked.

As described above, according to the present invention, an improved light source device for endoscopes may be provided capable of preventing the heat generation in incident end-face of the lightguide due to infrared light emitted from the light source, and emitting sufficient ultraviolet light and visible light.

The invention has now been explained with reference to specific embodiments. Other embodiments will be apparent to those of ordinary skill in the art. Therefore, it is not intended that the invention be limited, except as indicated by the appended claims, which form a part of this invention description.

What is claimed is:

1. A light source device for endoscopes for selectably applying fluorescent observation and reflection light observation with irradiation of blue to red visible light, said light source device comprising:
   a light source unit including a single light source, or a combined light source having a plurality of the single light sources; a wavelength control filter; a condensing means; and a lightguide, wherein
   the light source unit, the wavelength control filter, the condensing means and the lightguide are linearly arranged along an optical axis,
   light from the light source unit includes at least light of ultraviolet wavelength and light of visible and infrared wavelengths in the range of 400 to 650 nm when light from the light source unit is condensed at the light guide by the condensing means, and
   the wavelength control filter is arranged between the light source and the lightguide, and the wavelength control filter transmits at least light of ultraviolet wavelength and visible light wavelength in the range of 400 to 650 and blocks light of infrared wavelength, wherein the wavelength control filter satisfies the following conditions, $$T350 > 0.6 \quad (1)$$
$$T400\text{--}650 > 0.8 \quad (2)$$
$$T800\text{--}950 < 0.1 \quad (3)$$

where T350 is a transmission factor for 350 nm in wavelength, T400–650 is an average transmission factor for a wavelength range of 400 to 650 nm which is derived from averaging transmission factors measured in each 10 nm in a wavelength range of 400 to 650 nm, T800–950 is an average transmission factor for a wavelength range of 800 to 950 nm which is derived from averaging transmission factors measured in each 10 nm in a wavelength range of 800 to 950 nm.

2. A light source device for endoscopes as defined in claim 1, wherein the wavelength control filter is a transmission interference filter.

3. A light source device for endoscopes as defined in claim 1, wherein the wavelength control filter includes a transmission interference filter and a transmission absorption filter.

4. A light source device for endoscopes as defined in claim 1, wherein the wavelength control filter includes a transmission absorption filter and a transmission interference thin film provided on the surface of the transmission absorption filter.

5. A light source device for endoscopes as defined in either one of claims 2 to 4, which further includes a color separating filter provided between the light source unit and the lightguide.

6. A light source device for endoscopes as defined in claim 1, wherein the wavelength control filter includes three or more reflection surfaces, and is adapted to inflect the optical axis therein.

7. A light source device for endoscopes as defined in claim 6, wherein the wavelength control filter is a reflection interference filter.

8. A light source device for endoscopes as defined in claim 6, wherein the wavelength control filter includes a reflection interference filter and a transmission absorption filter.

9. A light source device for endoscopes as defined in claim 6, wherein the wavelength control filter includes a reflection interference filter and a transmission interference filter.

10. A light source device for endoscopes as defined in either one of claims 7 to 9, which further includes a color separating filter provided between the light source unit and the lightguide.

11. A light source device for endoscopes as defined in claim 1, wherein the light source includes a light emission part and a reflector.

12. A light source device for endoscopes as defined in claim 11, wherein the reflector has an ellipse shape.

13. A light source device for endoscopes as defined in claim 11, wherein the reflector has a parabola shape.

14. A light source device for endoscopes as defined in either one of claims 12 or 13, which further includes a color separating filter provided between the light source unit and the lightguide.

15. A light source device for endoscopes as defined in claim 1, wherein the light guide has an incident end-face, wherein the incident end-face is adjustably located at a position where ultraviolet light is condenses by the condensing means.

16. A light source device for endoscopes as defined in claim 1, wherein the light guide has an incident end-face, wherein when the transmission interference filter is arranged along the optical axis to allow fluorescent observation to be conducted, the incident end-face of the lightguide is adjustably located at a position where ultraviolet light is condenses by the condensing means, and when the transmission interference filter is spaced apart from the optical axis to allow visible light observation to be conducted, the incident end-face of the lightguide is adjustably located at a position where visible light is condenses by the condensing means.

17. A light source device for endoscopes as defined in claim 1, wherein the wavelength control filter is an interference filter including an amorphous thin film.

18. A light source device for endoscopes as defined in claim 1, wherein the interference filter is formed by laminating at least two groups of the amorphous thin films, wherein one group of the amorphous thin film has a light refractive index and includes at least one component selected from the group consisting of $Sc_2O_5$, $Ta_2O_5$, $HfO_2$ and $ZrO_2$, and another group of the amorphous thin film has a low refractive index and included at least one component selected from the group consisting of $SiO_2$ and $MgF_2$.

19. A light source device for endoscopes for selectably applying fluorescent observation and reflection light observation with irradiation of blue to red visible light, said light source device comprising:

a light source unit including a single light source, or a combined light source having a plurality of the single light sources; a wavelength control filter; a condensing means; and a lightguide, wherein the light source unit, the wavelength control filter, the condensing means and the lightguide are linearly arranged along an optical axis, light from the light source unit includes at least light of ultraviolet wavelength and light of visible and infrared wavelengths in the range of 400 to 650 nm when light from the light source unit is condensed at the light guide by the condensing means, and the wavelength control filter is arranged between the light source and the lightguide, and the wavelength control filter transmits at least light of ultraviolet wavelength and visible light wavelength in the range of 400 to 650 and blocks light of infrared wavelength, wherein the wavelength control filter satisfies the following conditions, $T350>0.8$ (4)

$T400–650>0.8$ (2)

$T800–950<0.1$ (3)

where T350 is a transmission factor for 350 nm in wavelength, T400–650 is an average transmission factor for a wavelength range of 400 to 650 nm which is derived from averaging transmission factors measured in each 10 nm in a wavelength range of 400 to 650 nm, T800–950 is an average transmission factor for a wavelength range of 800 to 950 nm which is derived from averaging transmission factors measured in each 10 nm in a wavelength range of 800 to 950 nm.

20. A light source device for endoscopes for selectably applying fluorescent observation and reflection light observation with irradiation of blue to red visible light, said light source device comprising:

a light source unit including a single light source, or a combined light source having a plurality of the single light sources; a wavelength control filter; a condensing means; and a lightguide, wherein the light source unit, the wavelength control filter, the condensing means and the lightguide are linearly arranged along an optical axis, light from the light source unit includes at least light of ultraviolet wavelength and light of visible and infrared wavelengths in the range of 400 to 650 nm when light from the light source unit is condensed at the light guide by the condensing means, and the wavelength control filter is arranged between the light source and the lightguide, and the wavelength control filter transmits at least light of ultraviolet wavelength and visible light wavelength in the range of 400 to 650 and blocks light of infrared wavelength, wherein the wavelength control filter satisfies the following conditions, $T350>0.6$ (1)

$T400–650>0.8$ (2)

$T800–1200<0.05$ (5)

where T350 is a transmission factor for 350 nm in wavelength, T400–650 is an average transmission factor for a wavelength range of 400 to 650 nm which is derived from averaging transmission factors measured in each 10 nm in a wavelength range of 400 to 650 nm, T800–1200 is an average transmission factor for a wavelength range of 800 to 1200 nm which is derived from averaging transmission factors measured in each 10 nm in a wavelength range of 800 to 1200 nm.

21. A light source device for endoscopes as defined in either one of claims 1 to 20, which further includes a means for blocking light of 330 nm or less in wavelength.

* * * * *